United States Patent
Hexsel (10) Patent No.: US 10,213,441 B2
(45) Date of Patent: *Feb. 26, 2019

(54) MEDICINAL COSMETIC LIPOATROPHY

(71) Applicant: Doris Hexsel, Porto Alegre (BR)

(72) Inventor: Doris Hexsel, Porto Alegre (BR)

(*) Notice: Subject to any disclaimer, the term of this patent is extended or adjusted under 35 U.S.C. 154(b) by 0 days.

This patent is subject to a terminal disclaimer.

(21) Appl. No.: 15/202,850

(22) Filed: Jul. 6, 2016

(65) Prior Publication Data

US 2016/0310510 A1 Oct. 27, 2016

Related U.S. Application Data

(60) Continuation-in-part of application No. 14/243,483, filed on Apr. 2, 2014, now Pat. No. 9,408,857, which is a division of application No. 13/810,022, filed as application No. PCT/BR2010/000059 on Mar. 2, 2010, now Pat. No. 9,220,717.

(60) Provisional application No. 61/209,065, filed on Mar. 2, 2009.

(51) Int. Cl.

| | |
|---|---|
| *A61K 31/58* | (2006.01) |
| *A61K 9/00* | (2006.01) |
| *A61K 31/167* | (2006.01) |
| *A61K 8/63* | (2006.01) |
| *A61Q 19/00* | (2006.01) |
| *A61K 8/42* | (2006.01) |
| *A61Q 19/06* | (2006.01) |
| *A61K 45/06* | (2006.01) |
| *A61K 31/137* | (2006.01) |
| *A61K 31/573* | (2006.01) |

(52) U.S. Cl.
CPC .............. *A61K 31/58* (2013.01); *A61K 8/42* (2013.01); *A61K 8/63* (2013.01); *A61K 31/137* (2013.01); *A61K 31/167* (2013.01); *A61K 31/573* (2013.01); *A61K 45/06* (2013.01); *A61Q 19/06* (2013.01); *A61K 9/0019* (2013.01); *A61K 2800/30* (2013.01); *A61K 2800/91* (2013.01)

(58) Field of Classification Search
None
See application file for complete search history.

(56) References Cited

U.S. PATENT DOCUMENTS

| | | |
|---|---|---|
| 6,395,294 B1 | 5/2002 | Peyman |
| 2005/0143347 A1 | 6/2005 | Boderke et al. |
| 2006/0127468 A1 | 6/2006 | Kolodney et al. |
| 2006/0154906 A1 | 7/2006 | Kolodney et al. |

OTHER PUBLICATIONS

Salam G.A. In American Family Physician 65:901-904, 905 (2002).*
'Kenalog' in www.rxlist.com/kenalog-10-injection-drug.htm (retrieved from the internet Oct. 30, 2014).*
Schectman, A.D. In American Family Physician 77(10):1372 (2008).*
Xylocaine at www.rxlist.com/ xylocaine-drug.htm (Retrieved from the internet Jan. 22, 2018).*
Epinephrine Definition at https://medical-dictionary.thefreedictionary.com/epinephrine (retrieved from the internet Jan. 22, 2018).*
Toyoyama et al. in Acta Anaesthesiol Scand 41(6):776-773 (1997).*
Trojian et al. in American Family Physician 2007:76:86-89.*
Amjad et al. in JCPSP 2005, 15(11), 683-685 (Year: 2005).*
Trojian et al. in American Family Physician 76(1), 2007, 86-89 (Year: 2007).*
Kang et al. in Dis Colon Rectum 2000:43:1288-1291 (Year: 2000).*
Nobutaka, in Scand J Plast Reconstr Hand Surg 33:89-91, 1999 (Year: 1999).*
Hexsel et al.: "Cosmetic lipotrophy of the face", Journal of the American Academy of Dermatology, C.V. Mosby, St. Louis, MO, US; vol. 60, No. 3, Mar. 2009 (Mar. 2009), p. AB185, XP025964614, ISSN: 0190-9622, DOI: 10.1016/J.JAAD.2008.11.805.
Donfrio et al: "Techniques in Facial Fat Grafting", Aesthetic Surgery Journal, Mosby-Yearbook, St. Louis, MO, US, vol. 28, No. 6, Nov. 1, 2008 (Nov. 1, 2008), pp. 681-687, XP025794998, ISSN: 1090-820X, DOI: 10.1016/J.ASJ.2008.09.003.
Arnold et al.: "Forty-nine years of meetings of the American Academy of Dermatology:1938 to 1987", Journnal of the American Academy of Dermatology, C.V. Mosby, St. Louis, MO, US, vol. 18, No. 4, Apr. 1, 1988 (Apr. 1, 1988), pp. 862-874, XP023331451, ISSN: 0190-9622, DOI: 10.1016/S0190-9622(88)80080-X.
Database Embase [Online], Elsevier Science Publishers, Amsterdam, NL; Nov. 2003 (Nov. 2003), Bak et al.: "A case of Multiple Angiolipoma", XP002684253, Database accession No. EMB/ 2004053744.
Korean Journal of Dermatology 200311 KR, vol. 41, No. 11, Nov. 2003 (Nov. 2003), pp. 1554-1556, ISSN: 0494-4739.
Paschoal, LH, Lourenco L, Ribeiro A, et al. Um alerta! Efeitos sistêmicos e teciduais da fosfatidilcolina em suínos [poster]. Presented at 16° Congresso Brasileiro de Cirurgia Dermatológica. Porto de Galinhas Jun. 2004.
New England J Med 2005;353:1711-23.
Patricia Guedes Rittes, The Use of Phosphatidylcholine for Correction of Lower Lid Bulging Due to Prominent Fat Pads, Dermatol. Surg. 2001;27: 391-392.

* cited by examiner

*Primary Examiner* — Dennis Heyer
(74) *Attorney, Agent, or Firm* — Lambert Shortell & Connaughton; Gary E. Lambert; David J. Connaughton, Jr.

(57) ABSTRACT

Methods relating to local or "intralesional" injections of corticosteroids are provided. More specifically injections of corticosteroids and preferably Triamcinolone and its derivatives are suitable to produce medicaments to be injected in the subcutaneous fat at deep levels to provoke to provoke cosmetic lipoatrophy of small fat deposits on the face and body.

20 Claims, 5 Drawing Sheets

MEDICINAL COSMETIC LIPOATROPHY

CROSS REFERENCE TO RELATED APPLICATION

This application is for entry into the U.S. National Phase under § 371 for International Application No. PCT/BR2010/000059 having an international filing date of Feb. 3, 2010, and from which priority is claimed under all applicable sections of Title 35 of the United States Code including, but not limited to, Sections 120, 363 and 365(c), and which in turn claims priority to Provisional Patent Application No. 61/209,065 filed on Feb. 3, 2009.

BACKGROUND OF THE INVENTION

Field of the Invention

The invention relates to a composition comprising at least one injectable corticosteroid and a diluent, preferable an anesthetic solution, which is suitable for producing medicaments to diminish small fat accumulations on the face and body by causing atrophy of the fat cells.

Description of Related Art

At present, subcutaneous accumulations of fat are treated by surgical procedures through liposuction or direct surgical removal. For small fat deposits, such those occurring with aging in some areas of the face, liposuction is too aggressive and is associated with the known complications or risks.

Injectable drugs, such as phosphatidylcholine (PPC) and sodium deoxycholate, also known as lipodissolve agents, were also used in some years ago (particularly in Brazil up to 2002), although there are no studies proving their safety and efficacy. Moreover, these drugs were also associated with severe side effects, including death in animals. (Paschoal L H, Lourenço L, Ribeiro A, et al. *Um alerta! Efeitos sistêmicos e teciduais da fosfatidilcolina em suínos* [poster]. Presented at 16° Congresso Brasileiro de Cirurgia Dermatológica. Porto de Galinhas June, 2004).

US2005/0143347 describes a method for removing subcutaneous accumulation of fat as well as aqueous preparations comprising at least one phospholipid and/or at least one bile acid and a component assisting degradation of fat such as riboflavin. Since the bile acids cause important inflammation where they are injected, an anti-inflammatory compound can be added in the preparation.

The term "corticosteroids" means compounds from the adrenal cortex. In technical terms, corticosteroid refers to both glucocorticoids and mineralocorticoids (as both are mimics of hormones produced by the adrenal cortex), but is often used as a synonym for glucocorticoid. Glucocorticoids are a class of steroid hormones characterized by an ability to bind with the glucocorticoid receptor (GR) and trigger similar effects. Glucocorticoids are distinguished from mineralocorticoids and sex steroids by their specific receptors, target cells, and effects.

Glucocorticoids have potent anti-inflammatory and immunosuppressive properties. This is particularly evident when they are administered at pharmacologic doses, but also is important in normal immune responses. As a consequence, glucocorticoids are indicated for the treatment of many different conditions, including allergies, autoimmune diseases and inflammatory disease like asthma (*New England J Med* 2005; 353:1711-23).

Corticosteroids can be used topically, orally and by injections. Injectable corticosteroids currently used in medicine include the short-Acting injectable corticosteroids such as cortisone and hydrocortisone; the intermediate-Acting Injectable corticosteroids such as Prednisone, Prednisolone tebutate, Triamcinolone and Methylprednisolone its derivatives such as methylprednisolone acetate; the long-Acting corticosteroids such as Dexamethasone and its derivatives such as Dexamethasone sodium phosphate and Betamethasone its derivatives such as betamethasone dipropionate, betamethasone disodium phosphate and betamethasone acetate, and others.

Triamcinolone and other systemic corticosteroids have strong anti-inflammatory effects and this explains the large use of these compounds in medicine. At Medline, more than twenty-five thousands papers are published on injectable corticosteroids and more than five thousands papers on triamcinolone are published. Injectable corticosteroids are usually commercialized in stable aqueous suspension and are also described in the patent applications or patents such as U.S. Pat. No. 6,395,294 owned by Triesence (exploitation by Alcon) until Jan. 13, 2020 for Triamcinolone acetonide in intravitreal injectable form.

Triamcinolone acetonide injectable suspension USP (Kenalog®-40 Injection, Bristol-Myers Squibb Company, Italy) is a synthetic corticosteroid designed to provide systemic immunosuppressant and anti-inflammatory effects, as well as other intralesional or sublesional local effects for various skin diseases and conditions. The drug is stable at room temperature and must be shaken well before using.

Triamcinolone and/or other injectable corticosteroids are commonly used in dermatology for intralesional injections, as well as in other specialties and diseases, such as for joint inflammation and pain. Intralesional corticosteroids injections release a high concentration of the drug directly on the action site, with minimal systemic absorption. These drugs are considered very safe, low cost and efficient for an expressive number of diseases and conditions, for patients of different ages. Few applications and low doses are considered extremely safe, also for patients presenting severe diseases.

The aging process is caused by intrinsic and extrinsic aging, as well as changes in hard and soft tissues. Muscular hyperactivity causes dynamic wrinkles, currently treated by botulinum toxins. The losses in hard and soft tissues are currently being treated by fillers. The surface alterations are being treated by ablative and non-ablative techniques, as well as by topical retinoids and other active ingredients. There are no currently medical approved drugs for age-related fat accumulations on the face and beyond, except deoxicholate for submental fat. It was also reported that fat pads like those occurring under the eyes, on the abdomen or on the hips can be treated by phosphatidylcholine and people who received subcutaneous injection of Lipostabil® N I.V. showed esthetic improvements in their appearance. (Patricia Guedes Rittes, *The Use of Phosphatidylcholine for Correction of Lower Lid Bulging Due to Prominent Fat Pads*, Dermatol. Surg. 2001; 27: 391-392). Residual small fat deposits are also common complaints after liposuction.

Thus, the term "age related fat deposits" of the face are the ones to be treated according to the present invention. These fat accumulations were located in the face as following: under the eyes, pre-jowl fat and submental fat.

However, a new compound approved in the US use the deoxycholate, marketed as Kibella® by Allergan. US2005/0261258 proposes compositions and methods useful in the non-surgical removal of localized fat deposits in patients in need thereof using pharmacologically active detergents are disclosed. The deposit is contacted with a composition consisting essentially of an effective amount of up to 5% deoxycholic acid or salt thereof and an excipient wherein said deoxycholic acid or salt thereof is a sole fat removing component. Even if efficient, this product is known as being painful during the injection. There is a need to find a new product that could be efficient in reducing the fat without cause any kinds of discomfort or pain in the patient. Furthermore, it is important to mention that Kibella is not recommended for age related fat deposits, but for (exclusively) submental fat.

SUMMARY OF THE INVENTION

In the attempt to find effective compounds for nonsurgical removal of subcutaneous accumulations of fat of the face and beyond, it has now surprisingly been found that subcutaneous administration of Triamcinolone and/or other corticosteroids, at low doses and few applications, which have to date been used for many diseases and conditions, also lead to a safe and effective regression of small fat deposits in the face and small areas of the body.

The invention therefore relates to the use of a composition comprising:
a) at least one corticosteroid
b) optionally at least one anesthetic solution; and
c) a saline or physiological pH solution
for producing a medicament to reduce small areas of subcutaneous accumulations of fat.

In an alternative and preferred embodiment, the invention relates to the use of a composition comprising:
a) at least one corticosteroid;
b) optionally at least one anesthetic solution; and
c) a physiologically and pharmaceutically acceptable vehicle, in which the corticoid remains stable
for producing a medicament to reduce small areas of subcutaneous accumulations of fat.

In the context of the present invention, the composition may comprise more than one corticosteroid and for example two or more in combination in the same physiological medium.

The invention further relates to the use of a composition comprising:
a) at least two or more corticosteroids
b) optionally at least one anesthetic solution and
c) a physiologically and pharmaceutically acceptable vehicle
for producing a medicament for reduce small areas of subcutaneous accumulations of fat.

DETAILED DESCRIPTION

The invention further relates to the use of the compositions for producing a medicament for the treatment of small fat accumulations on the face and body, including residual areas of liposuction and other localized fat accumulation.

The invention further relates to the use of the compositions for producing a medicament for the treatment of derangements of fat distribution of an unwanted nature, such as raised areas of cellulite and fat related tumors.

One embodiment of the present invention is a method of decreasing or reducing small fat deposits by administering to an individual in need thereof, a sufficient amount of a composition comprising at least one injectable corticosteroid with a physiologically and pharmaceutically acceptable vehicle. In a preferred embodiment the said composition is administered to an individual in need by local injections in the subcutaneous fatty areas.

By physiologically acceptable vehicle it is meant a medium compatible with intralesional or subcutaneous injection. This medium can be prepared in advance or in a way that it can be prepared immediately before use.

By pharmaceutically acceptable vehicle, it meant a physically and chemically stable composition over time, compatible with the active ingredient, and with the injectable way of administration.

By diluent it is meant any acceptable diluent of the injectable corticosteroid which is preferably 0.9% saline or saline plus anesthetic solution or anesthetic solution alone. Injectable anesthetic solutions as diluent are preferable to make the procedure less painful. The most frequent anesthetic solutions have 1% to 2% lidocaine as the active ingredient, but bupivacaine and others may also be used.

According to the invention, through the use of the compositions it is possible to avoid the abovementioned risks and side effects of surgical treatments and those arising from injectable lipodissolve agents at the currently used doses. In addition, this is a minimally invasive, outpatient treatment, showing great cost-effectiveness, and less painful than the existing products.

Contraindications for the use of systemic corticosteroids include diabetes, infectious illness, HIV, psychiatric disorders, SAH and other specific conditions.

Studies show that small doses of systemic corticosteroids for short periods of time can be considered safe, in patients without the above contra-indications. The doses for local injections (e.g. intra-articular, intrabursal, intradermal, intralesional) are given as ranges only. A safe dose of Triamcinolone is less than 0.15 mg/kg. The actual dosage depends upon the size of the joint of lesion and the severity of the condition being treated.

The safer use of corticosteroids refers to less than 1 week on the recommended doses. Frequent applications and high doses of these compounds can cause systemic side effects. Even small doses, if used for long periods of time can also cause systemic side-effects. However, in the present invention a sufficient safe dose from 1 to 10 mg of Triamcinolone in the composition will be used in 3 consecutive months and then this is a safe method of treatment.

Although the benefits of glucocorticoid therapy are derived from short-term vascular changes and limited immunosuppression, prolonged or high-dose glucocorticoid therapy has multiple side effects (*Pharmacol Ther* 2002; 96: 23-46). Glucocorticoid treatment can cause hypertension by two distinct mechanisms: one involves renal sodium retention and the ensuing increase in blood volume; a second results from potentiation of vasopressor responses to angiotensin II and catecholamines (*Cardiovas Res* 1999; 41:55-64). Even inhaled glucocorticoids are absorved by the circulatory system and still cause side effects such as a decreased growth rate in children (*J Allergy Clin Immunol* 2003; 112:Suppl 3:s1-s40; Arch Inter Med 1999; 159:941-55).

The most known side-effects of the oral and parenteral use of corticosteroids are gland adrenal atrophy, cushing's syndrome, dyslipidemia, hypertension, thrombosis, vasculitis, changes in behavior, cognition, memory, and mood (i.e., glucocorticoid-induced psychoses), cerebral atrophy, gastrointestinal bleeding, pancreatitis, peptic ulcer, activation of latent viruses, opportunist infections, delayed wound healing, erythema, hypertrichosis, perioral dermatitis, petechiae, glucocorticoid-induced acne, striae rubrae distensae, telangiectasia, skin atrophy (including single injections of triamcinolone on dose of 10 mg or 25 mg hydrocortisone), bone necrosis, muscle atrophy, osteoporosis, retardation of longitudinal bone growth, cataracts, glaucoma delayed puberty, fetal growth retardation, hypogonadism (*New England J Med* 2005; 353:1711-23; *British Journal of Rheumatology* 1991; 30:39-44).

Recently, a review showed that the side effects of short-term oral corticosteroids such as vascular necrosis and a few cases of fatal varicella-zoster can occur in immunocompetent patients. Severe mood changes and psychotic reactions rarely occur unpredictably with short-term corticosteroids. These events are rare, and most treatments with short-term corticosteroid therapies are problem free. The literature reviewed clearly indicates that a short course of corticosteroids of 1 week, in the absence of specific contraindications, is unlikely to be harmful (psychotic or prepsychotic episodes possibly excepted (*J Cutan Med Surg*. 2008; 12(2): 77-81).

Triamcinolone acetonide has been used as intravitreal injection with some complications like infectious endophthalmitis, transient central retinal artery occlusion, conjunctival ulcerations, retinal detachment and potential reactivation of a cytomegalovirus retinitis and posterior subcapsular cataract (*Ophthalmologe*. 2004 February; 101 (2):121-8., *Ophtalmol*. 2008 September; 31(7):693-8; *J Drugs Dermatol*. 2008; 7(8):757-61). Intralesional triamcinolone acetonide has been used extensively for the treatment of hypertrophic and keloid scars. Complications are few, usually being local skin color changes, prominent vascular markings, or subcutaneous atrophy. Although, cushing's syndrome following intralesional administration of triamcinolone acetate has already been described (*Ann Plast Surg* 1996 May; 36(5):508-11).

The terms "local injections" or "intralesional injections" means injections applied into a specific area, condition or lesion. However, the administration of corticosteroids in the context of the invention is injected into the fat that are located in the subcutaneous in the human faces and around them, as well as in small areas of the human bodies. Despite the known side effects of the corticoid described above, It has been found that the invention keeps the injections in a safe way, by using a maximum total dose recommended per session of 10 mg, once a month for three (03) consecutive months. This regimen allows to obtain a surprising efficacy with no safety and pain issue.

Not only acetonide but also other forms of Triamcinolone, such as hexacetonide, can be used for parenteral and/or intralesional and/or subcutaneous injections. Short-acting injectable corticosteroids are preferable to be use in this medical indication.

Side effects of intralesional injections of Triancinolone and other injectable corticosteroids in dermatology include skin discoloration, skin atrophy and risk of systemic side-effects, when high doses and frequent injections of this compound are used. Pariser and Murray described a greater risk of cutaneous atrophy with concentrations above 5 mg/cm$^3$ of triamcinolone acetonide (Pariser H, Murray P F. *Intralesional Injections of Triamcinolone. Effects of different concentrations on psoriatic lesions. Arch Dermatol.* 1963 February; 87:183-7). It is important to mention that the present application will produce a medicament using 2 mg/mL or 2 mg/cm not 5 mg/cm$^3$, which causes cutaneous atrophy.

Injections into the superficial dermis can also result in initial epidermal sloughing and persistent epidermal atrophy, whereas those in the deep dermis and subcutis may result in variable loss of fat with minimal epidermal change (Donofrio L M. *Panfacil volume restoration with fat. Dermatol Surg* 2005; 31: 1496-1505).

Besides skin atrophy, skin side effects arising from intralesional injections on the skin and/or subcutis include skin discoloration, asymmetries and volume reductions with consequent sagging of the suprajacent skin. When the applications are done to the subcutaneous fat, these local side effects are mainly related to the technique and superficial injections. The risks of local side effects, such as skin necrosis and atrophies are rare. Local atrophy may be wanted only for the fat tissue but not to the skin (epidermis and dermis).

The term "local anesthetic" means injectable and/or topical compounds. The Injectable anesthetic compounds are selected from mepivacaine, bupivacaine, ropivacaine. Chloroprocaine, procaine, articaine/epinephrine and lidocaine can be used as a diluent. Topical anesthetic creams or a cooler are also used to reduce the pain of the injections.

For the treatment of localized fat, the reasonable average recommended dose of Triamcinolone diluted in local anesthetic solution is 1 mg to 10 mg per month for 3 months.

In one embodiment, the compositions can be made extemporaneously just before injection. The compositions of the invention are produced, for example, by dissolving 0.05 mL of Triamcinolone acetonide (40 mg/mL) and 1 mL of lidocaine. It is important to mention that the doses injected into the fat are safe and do not cause skin atrophy.

The solution or dispersion containing the active drug (corticosteroids) is usually concentrated, and then a diluent is added to increase the dilution. In an alternative embodiment, the anesthetic solution is added as a diluent or in replacement of the diluent to increase the dilution and make the treatment more comfortable for the patients. Production of the compositions of the invention is currently done at the moment of application.

Alternatively, the solution or dispersion containing the active drug (corticosteroids) in a proper safe dose is appropriately diluted at the physician's discretion. The physician can choose to add or not to add the anesthetic solution.

Simultaneous introduction of the compositions and pharmaceutical forms employed according to the invention can also take place in particular applications via tumescence method, which makes use of the hydrostatic pressure in order to ensure uniform distribution and to increase the safety and efficacy of the procedure. These can be achieved by dissolving the preparations of the invention in higher volumes of saline and/or other necessary pharmacological agents. Variations on the technique can also be done, by preceding the injection of the active drug (triamcinolone or similar) by local tumescent anesthesia.

The composition(s) employed according to the invention, and comparable pharmaceutical forms, are administered by subcutaneous injections on the fat, also called "local" or "intralesional" injections. Subcutaneous injections at deep level are preferred for cosmetic lipoatrophy and prevent skin atrophy.

In the context of the present invention, additional ingredients can be added to the formulation.

The composition(s) employed according to the invention, and comparable pharmaceutical forms, are administered by subcutaneous injections on the fat, also called "local" or "intralesional" injections. Subcutaneous injections at deep level are preferred for cosmetic lipoatrophy and prevent skin atrophy.

Suitable preparations and pharmaceutical forms can be suspensions, emulsions or injectable solutions, and products with protracted release of active ingredients. In order to increase the stability of the compositions and pharmaceutical forms of the invention, the preparations can also be in the form of a concentrate, dry substance or lyophilizes.

These pharmaceutical products are preferably produced and administered in dosage units, each unit comprising a particular dose of the composition(s) of the active ingredient. In the case of solutions for injection in ampoule form, this dose can be adjusted, preferably from about 2 mg to 10 mg of Triancinolone acetonide, or equivalent doses of other injectable corticosteroids.

Monthly doses of solutions for injection required for the treatment of an adult patient are, depending on the size of the treated adipose tissue, from 1 mg to 10 mg, preferably 2 mg to 5 mg of Triamcinolone acetonide, or equivalent doses of other injectable corticosteroids.

In one embodiment, the composition may comprise Triamcinolone acetonide and lidocaine in a solution without the presence of a vasoconstrictor. Quantities of Triamcinolone acetonide and lidocaine may vary in different formulations even keeping the same concentration. However the compositions can have a quantity from 1 mg to 10 mg, preferably 2 mg to 4 mg of Triamcinolone acetonide, or equivalent doses of other injectable corticosteroids. In a particular embodiment, the quantity in the composition for injection may be approximately 4 mg of Triamcinolone acetonide, along with lidocaine. In another embodiment, the quantity in the composition for injection may be approximately 4 mg of Triamcinolone acetonide, along with lidocaine. The quantity of lidocaine in currently approved forms also vary from usual concentrations of 0% to 2%.

In one embodiment, the Triamcinolone acetonide may be diluted in 1 ml of 1% (0.01 g lidocaine/mL solution) or 2% lidocaine solution (0.02 g lidocaine/mL solution). In a particular embodiment, the injectable composition of the solution of Triamcinolone acetonide has a concentration of 2 mg Triamcinolone acetonide per 1 (one) ml of injectable composition solution.

One embodiment of a treatment regimen may include injection of a composition of 4 mg of Triamcinolone acetonide in 2 ml of 1% or 2% lidocaine solution. This injection can be performed once a month for three consecutive months.

Another embodiment of a treatment regimen may include injection of a composition of 2 mg of Triamcinolone acetonide in 1 ml of 0% to 2% lidocaine solution. This injection can be performed once a month for three consecutive months. However, this regimen, quantity of Triamcinolone acetonide in the injectable composition may vary depending on patient needs up to a total dose of 10 mg/month that is considered safe. In some treatments, quantities of Triamcinolone acetonide may be increased from 1 mg to 10 mg, typically depending on the size of area of the fat deposit that is being treated. For example, the total dose of Triamcinolone can vary but the concentration remains the same, as indicated below. In this sense, if larger areas will be treated, more points of the composition proposed will be injected and consequent higher dose of the effective drug, the Triamcinolone. For example, the doses can vary as indicated below:

2 mg Triamcinolone in 1 ml solution of 0% to 2% lidocaine 4 mg Triamcinolone in 2 ml o solution of 0% to 2% lidocaine 6 mg Triamcinolone in 3 ml solution of 0% to 2% lidocaine 8 mg Triamcinolone in 4 ml solution of 0% to 2% lidocaine 10 mg Triamcinolone in 5 ml solution of 0% to 2% lidocaine In this manner, we can stablish a fix dose per point to be injected in the patient. If the area is larger, more injection points, that mean more volume and consequent higher dose, can be injected. If the patient has a little volume of fat to be decreased, such as eyelid bags, 0.5 ml of the composition would be fine. If the patient has larger area, he/she may need 4 ml and more injection points to be safe the procedure.

In the above noted embodiment comprising only Triamcinolone acetonide and lidocaine in the composition according to the invention, the active ingredient causing fat atrophy is the Triamcinolone acetonide. Further, in some cases, patients have relative contra-indications for vasoconstriction agents. For example, vasoconstriction agents may be problematic for those having high blood pressure. In initial testing, this composition embodiment was used with the aim to keep the drug in the injected areas. However, similar results were found when the vasoconstrictor agent was not in the formulation. Vasoconstriction agents allow for an increase in the amount of lidocaine used. However, the injection quantities and composition of this embodiment composition require only a small quantity of lidocaine, below the accepted 4 mg/kg bodyweight, and therefore a vasoconstrictor is not need.

It is worth noting that in the prior art, the use of Triamcinolone acetonide or other anti-inflammatory corticosteroids in facial injections were not used for the purposes of causing fat atrophy, but instead to minimize inflammation caused by injection of deoxycholate. This demonstrates that it was not known in the prior art to use Triamcinolone acetonide as an active ingredient to treat facial fat deposits by causing fat cell's atrophy.

Suitable preparations and pharmaceutical injectable forms can also be diluted before administration, preferably with saline solution, having in mind that will be delivered always a fix safe dose per point of injection. However, in some circumstances, higher or lower monthly doses may also be appropriate. The doses also depend on the area to be treated, the disease, condition or amount and/or thickness of the fat tissue to be treated, always keeping the same safe concentration of the drug. For this reason, larger areas will demand more injection points e consequently higher dose.

Administration of the monthly dose can take place both through a single dose in the form of a single dosage unit or else a plurality of small dosages units per points of injection in a specific area to be treated.

The term "subcutaneous derangements of fat distribution" means adipose tissues in the body of humans and animals which occur as genetically related or food-related depot of fat in the form of anatomic localized fat pads and can be regarded as esthetically disturbing critical zones such as abdomen, buttocks, hips, knee, calves, thighs, upper arm, chin, cheeks. They may also involve dystrophic proliferations of adipocytes such as benign proliferations of the fat cells like that occurring in lipomas.

The term "small localized area of fat accumulation" means all areas, from 10 cm$^3$ up to 30 cm$^3$, of fat localized on the face or body that occurred due to an increase in the number or size of the fat cells. These include the fat in the perioral area, eyebulging, submental, preaxillary fat, small raised areas in the abdomen and/or dorsum and love handles, raised areas on the buttocks, as well as excess response from surgical procedures such as liposuction and Subcision. These are usually considered cosmetic defects.

The term "adipocyte's atrophy" means decrease in the size and/or number of adipocytes as shown by skin biopsies. This adipocytes' atrophy leads to reduction of the treated small localized fat deposits.

This patent reported a new potential use of local injections of triamcinolone, also called "local" or "intralesional injections", to induce cosmetic lipoatrophy of small-localized fat deposits by reducing the size of the adipocites and fat thickness. This is a fast, efficient, cost-effective and low risk procedure, useful for cosmetic proposes.

Figure 1:
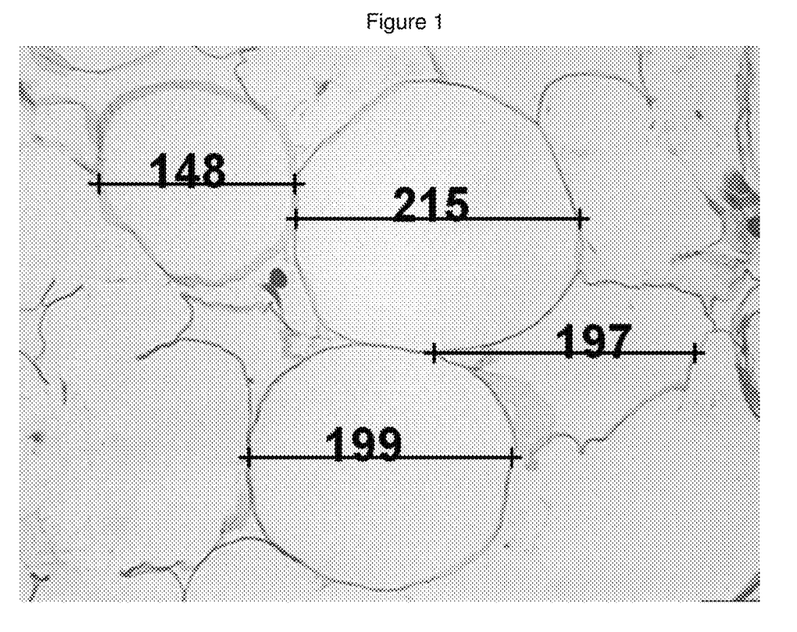
FIG. 1 provides a histologic picture that shows fat tissue with hematoxilyn-eosin stain before treatment and the measurements of some adipocyes in pixels using same magnification.

Turning now to FIG. 1, a histologic picture is provided which shows fat tissue with hematoxilyn-eosin stain before treatment and the measurements of some adipocyes in pixels using same magnification.

Figure 2:
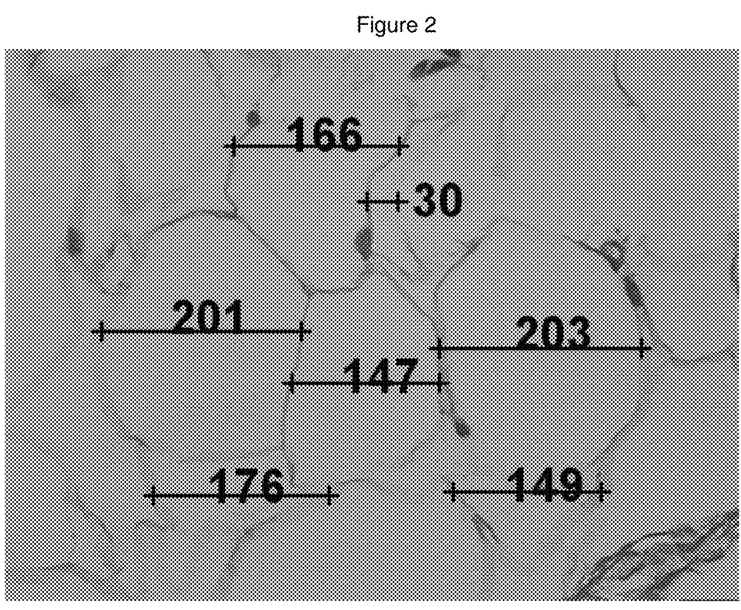
FIG. 2 provides a histologic picture that shows fat tissue with hematoxilyn-eosin stain after treatment and the measurements of some adipocyes in pixels using same magnification.

FIG. 2 is a histologic picture which shows a sample of fat tissue of the same area as FIG. 1, resulting from skin biopsy one month after single treatment with Triamcinolone local injections. There is a reduction on the average of the diameter of the adipocytes in the treated area.

FIGS. 1 and 2 show morphometry performed at the biopsies of the suprapubical area treated with a single injection of triamcinolone, before (FIG. 1) and one month after (FIG. 2). The average number of adipocytes observed in the optical field at the same magnification increased from 4 to 7 adipocytes per field. This is because the size of adipocytes decreased. The average area of the adipocytes reduced from 31661 to 21705 pixels and their average diameters reduced from 190 to 153 pixels.

Figure 3:
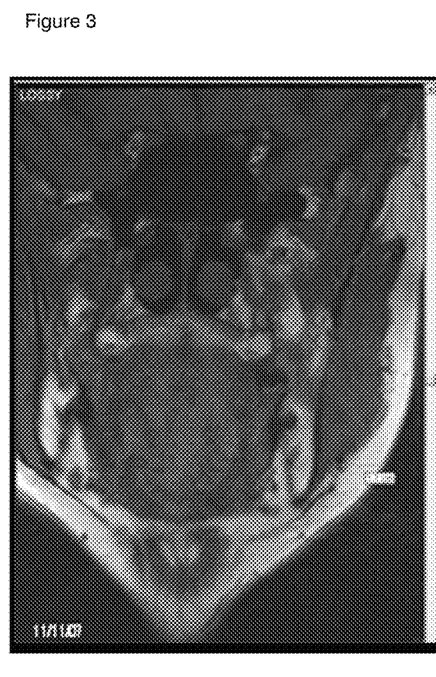
FIG. 3 provides a view of an MRI exam performed before a single session of treatment with triamcinolone injections.
Figure 4:
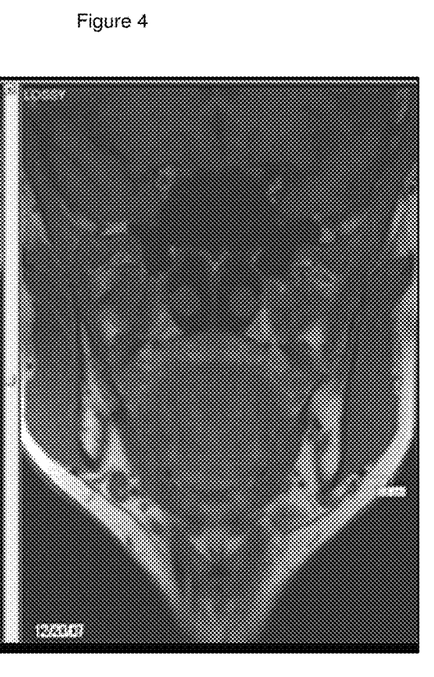
FIG. 4 provides a view of an MRI exam performed after a single session of treatment with triamcinolone injections.

FIGS. 3 and 4 refer to MRI exams performed before (FIG. 3) and after (FIG. 4) single session of treatment with triamcinolone (TA) injections. There was a reduction of 27.3% of the thickness of the study area of facial fat before (1.1 cm) and after (0.8 cm) treatment.

Figures 5, 6:
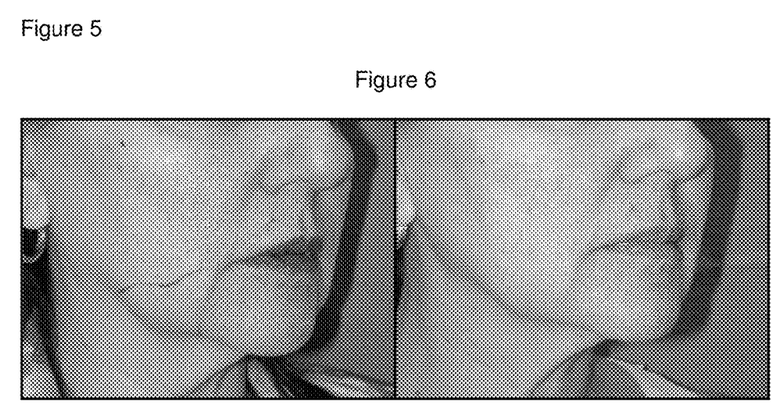
FIG. 5 provides a view of a patient with marked areas for injection treatment, before treatment.
FIG. 6 provides a view of the same patient with marked areas for injection treatment one month after a single session.

FIGS. 5 and 6 show the same patient with marked areas for TA injections, before (FIG. 5) and one month after (FIG. 6) single session of TA injections.

Figure 7:
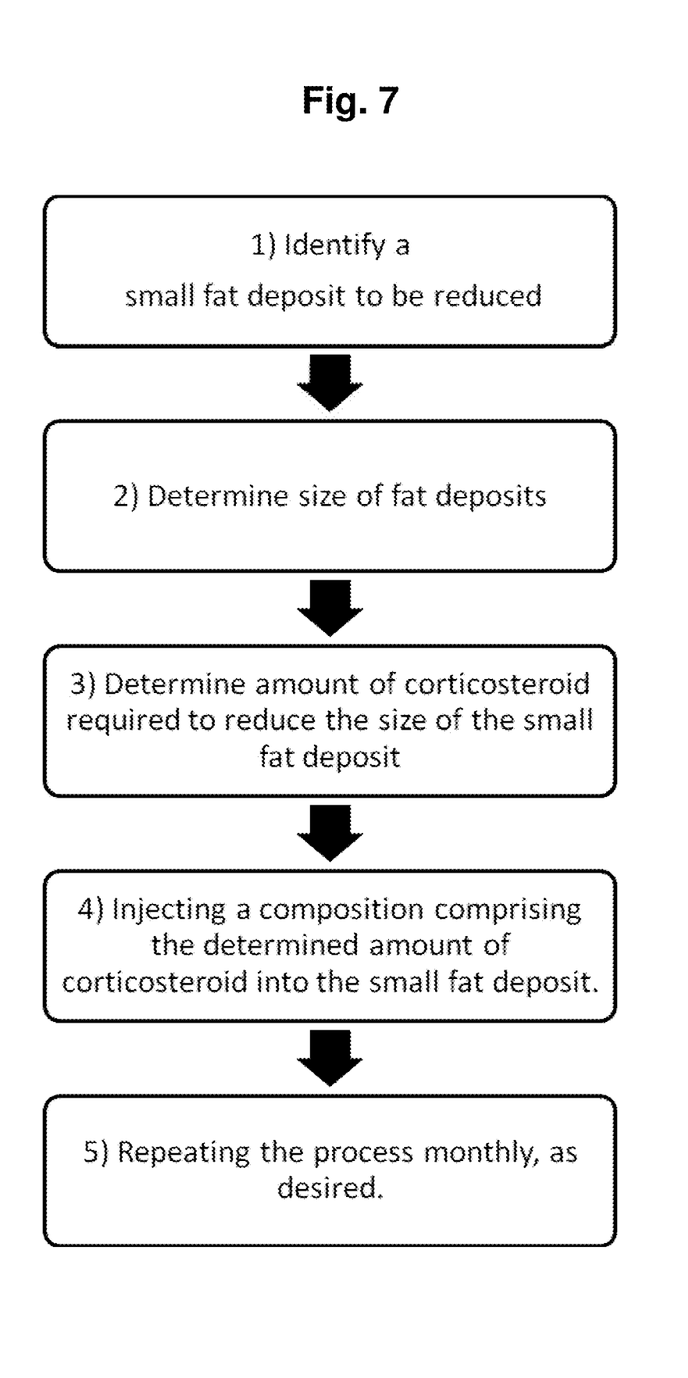
FIG. 7 provides a flow chart of an embodiment of the steps involved in the method of treatment.

FIG. 7 provides a flow chart of steps involved in an embodiment of treatment. The treatment begins by identifying a small fat deposit or a number of fat deposits to reduce by the treatment. The size of these fat deposits may be then determined. Next, an amount of corticosteroid is determined to reduce the size of the identified fat deposits. Once determined, a composition is injected into the fat deposit, the composition comprising the determined amount of corticosteroid, and optionally other components as described herein. This process may be repeated, for example, monthly, to maintain reduction of the fat deposits.

The present invention is described by the following example, which is one of several embodiments.

Example 1

A retrospective sample of treated patients is presented with the objective to describe a new therapeutic modality to treat small-localized fat areas of the face, which interfere with youth and beauty of the face. Moreover, there is the need for minimally invasive treatments to safely treat small areas of localized fat on the face.

Research Design and Methods

A series of cases of small localized fat deposits on the face were treated with local triancinolone from March 2005 to October 2008 at a private clinic in Porto Alegre, southern of Brazil. Fifty-six female patients with localized fat areas of the face were included in this sample. They received injections of triamcinolone (Kenalog®-40 Injection) diluted in anesthetic solution (0.02 g/mL Lidocaine plus 0.0004 g/mL Phenilephrine—Novocol®), in different doses and number of applications (up to 3 injections, once a month), according to patient's needs. The areas treated were the pre-jowl and submental areas, and, the inferior eyelids. Patients received injections in these fatty areas of the face, through a 0.3 cc BD Ultra Fine II syringe with short needle of minimum 7 or 8 mm long. All the injections were performed at the subcutaneous, 4 to 7 mm below the cutaneous surface. Small volumes (0.01 to 0.02) of the diluted triamcinolone were injected at 1 cm apart at the treated areas.

One patient was submitted to a facial Magnetic Resonance Imaging (MRI) exam before and after the triamcinolone injections, in order to show the results in terms of the changes in the thickness of subcutaneous tissue. Magnetic resonance imaging examination was performed with 1.5 Tesla Closed Bore Scanner (Magnetom Symphony Maestro Class, Siemens, Erlangen, Germany) with dedicated flexible coils. T1-weighted (600 ms/14 ms, Time Repetition/Time Echo) and T2-weighted (2500 ms/45 ms, TR/TE) turbo spin echo sequences were performed in coronal, axial and sagittal planes, with emphasis on the sagittal plane. An experienced radiologist evaluated the MRI images. The thickness of SQ adipose tissue was measured with Syngo software (Siemens, Erlangen, Germany) in millimeters (mm).

Another patient was submitted to 3 mm punch biopsies (one on the submental area and another on suprapubical area) before and after single treatment. Histological specimens of SQ tissue were stained with hematoxylin and eosin (HE stain) and flow citometry was also performed in the histological images of before and after treatment samples.

Medical records included the main surgical cosmetic procedures carried out in association with triamcinolone injections, at the private dermatological clinic where the study took place.

The records of 56 patients with localized fat areas on the face that were treated with triamcinolone injections diluted in an anesthetic commercial composition were reviewed retrospectively. All patients were Caucasians women and the average of age was 57, 2±12, 2 years. Demographic data and characteristics of the triamcinolone applications were obtained from the clinical files, highlighting the main application areas, the dilution of the drug and the number of sessions. These data is presented in Table 1.

TABLE 1

Demographic data from 56 patients treated with Triamcinolone injections.

| Groups | Number of subjects | Age (years)* | Average dose (mg) of triamcinolone (per session) | Average of volume (mL) administered of diluted triamcinolone | Average of volume of Anesthetic solution in the composition | Proportion of triamcinolone: and Anesthetic solution |
|---|---|---|---|---|---|---|
| Mandibular Area | 37 | 59 ± 12 | 5.2 | 0.13 | 0.27 | 1:2.1 |
| Submental Area | 11 | 52 ± 08 | 4.8 | 0.12 | 0.2 | 1:1.7 |
| Inferior Eyelids | 8 | 55 ± 16 | 3.2 | 0.08 | 0.16 | 1:2 |

*Age was described in average ± Standard deviation.

Regarding the frequency of injections, they were performed as follow: one session for submental area; one or two sessions for infraorbital area (62.5% of this group of patients were submitted to one session, whereas 37.5% were submitted to two sessions); one to three sessions for the mandibular area (70.3% of this group of patients were submitted to one session, 27% were submitted to two sessions, and only 2.7% were submitted to three sessions).

Fifty seven percent of the patients underwent to another cosmetic procedure performed in the same day and surgical session. These patients received the triamcinolone injections and 30.3% received also fillers; 16% received also Botulinum Toxin (BT) and 10.71% received both (fillers and BT) combined with the Triamcinolone injections.

Twenty-nine subjects (51.78%) returned to the clinic for evaluation. All of them were very satisfied with the results of the procedure and did not presented serious adverse events. The physician who evaluated these subjects considered that they had good clinical and cosmetic improvement of facial contour due to reduction of the fatty areas, as shown in the before and after figures (FIGS. 4 and 5). Twenty-seven patients have not returned for evaluation yet, so subject satisfaction and clinical improvement are missing.

High-resolution MRI images performed in the axial plane demonstrated that there was significant reduction of the SQ adipose tissue at the treated area (mandibular). The reduction of the fat thickness showed by MRI was 37.5% at the mandibular area (from 0.8 to 0.5 cm) and 33.3% at the submental area (from 0.6 to 0.4 cm) (FIGS. 3 and 4).

Histological analysis demonstrated about 30% reduction in the volume of adipocytes in the sites of the injections, as shown in the before and after single treatment biopsies. Flow citometry results showed reduction in the average of the diameters of the adipocytes increase of the number of the adipocytes that were visualized per field at the same magnification field (from 4 to 7). (FIGS. 1 and 2)

A few local side effects were observed in this group of the patients. The majority of the patients had pain and slight erythema during and immediately after the injections. Many patients presented hematomas in variable number and size, which disappeared spontaneously in a few days. No severe local or systemic side effects were observed in the patients treated with this new technique. No lab exams were done to evaluate potential systemic absorption of the drugs.

Cosmetic local side effects were presented by three patients, as described below:

One case of skin relief depression in the lower eyelid that appeared 2 months after the injection. No treatment was given and it disappeared spontaneously after 1 months;

One case of skin and subcutaneous atrophies, caused by accidental superficial injections. This happened due to continuous talking by the patient during injections at the mandibular area. This was corrected with small volumes of an hyaluronic acid filler injections (Restylane—Q-Med);

One case compliant of increased laxity of the mandibular skin was noted, although this patient never complained about this. This can be treated by radiofrequency of Infra-red light, as well as poly-L lactic acid;

One case of asymmetry of the anterior fatty areas of neck. This was corrected with a second session of triancinolone injections. Sub-optimal response may also occur.

The indication for only few monthly injections of the composition aims to prevent prolonged use and risk of systemic effects of corticosteroids.

Example 2

Another retrospective sample of treated patients will be performed with the objective to describe a new therapeutic modality to treat small localized fat areas of the face, this one without include vasoconstrictor agents in the composition reaching efficiency and safety methods to reduce small fat deposits.

Research Design and Methods

The trial include participants between 40 and 65 years of age. All of participants have medical history and physical exam, which do not interfere with the trial. The study includes participants who present fat accumulations in the submental and pre jowl areas.

20 trial participants will receive triamcinolone acetonide diluted into an anesthetic solution containing only lidocaine, and 20 participants will receive triamcinolone acetonide diluted into an anesthetic solution containing lidocaine plus a vasoconstrictor. A control group will also be evaluated in this study. Three monthly treatment sessions will be held.

Product dilution for the treatment will be 2 mg of Triamcinolone per ml which means a volume of 0.05 ml of Triamcinolone (Kenalog 40 mg/m) plus 0.2 mL of lidocaine anesthetic solution (0.02 g/ml or 2% Lidocaine) without a vasoconstrictor agent, 0.75 ml of sterile saline solution will be added to the solution, creating a solution with an approximate concentration of 2 mg/mL of triamcinolone.

An experienced dermatologist (the inventor) will carry out the dilutions and apply the injections. The total volume injected and the number of injection points will vary according to the clinical indication for each trial participant, in order to achieve the best individual results. The injected volume per point will vary from 0.02 to 0.04 ml. The following definitions will be followed for all three treatment sessions:

the participants with pinch thickness up to 0.5 cm, as measured by the caliper or plicometer, during the initial visit will receive a total volume of 0.5 mL of solution (1 mg of triamcinolone) distributed at points 1 cm apart in the submental and pre jowl areas, posterior to the melomental fold;

the participants with pinch thickness up to 1 cm, as measured by the caliper, will receive a total volume of 1 ml of solution (2 mg of Triamcinolone) distributed at points 1 cm apart in the submental and pre jowl areas, posterior to the melomental fold.

the participants with pinch thickness up to 1.5 cm, as measured by the caliper, during the initial visit will receive a total volume of 1.5 ml of solution (3 mg of triamcinolone) distributed at points 1 cm apart in the submental and pre jowl areas, posterior to the melomental fold;

participants with pinch thickness up to 2 cm, as measured by the caliper, during the initial visit will receive a total volume of 2 ml of solution (4 mg of triamcinolone) distributed at points 1 cm apart in the submental and pre jowl areas, posterior to the melomental fold;

For each 0.5 cm of pinch thickness as measured by the caliper, another 0.5 mL of solution will be added, up to the maximum dose of 10 mg.

A total of three applications will be made (during visits two, three and four) with a 3 to 4 week interval between each visit. The drug will be administered in the morning, in order to avoid interfering with the pituitary-adrenal axis. The dose of 8 mg of triamcinolone corresponds to 1.5 mg of dexamethasone. A very similar dosage is used during Cushing's system tracking tests (1 mg of dexamethasone taken when going to bed) which poses no risk the patient and is widely used in clinical practice.

The laboratory exams will be carried out to verify the safety of the procedure: blood exam, platelets, serum creatinine, serum urea, transaminases, prothrombin time (PT), activated thromboplastin time (KTTP), serum cortisol, adrenocorticotropic hormone (ACTH) and fasting blood glucose.

CONCLUSION

The subcutaneous fat face is partitioned into discrete anatomic compartments: nasolabial fat, cheek fat, forehead and temporal fat, orbital fat and jowl fat.

A youthful face is characterized by the fullness and a smooth transition between subcutaneous compartments characterize a youthful face. Facial aging is partially characterized by how the fat compartments change with age. Aging leads to abrupt contour changes between these regions, by volume loss and malposition of these compartments, in a number of causes[11]. A youth face looks like a triangle with its base up. In aged face, fat accumulation around the mandibular bone looks like a triangle with the base down.

Rare studies address solutions for the aged related facial fat deposits, which are a frequent complaint, and increase skin sagging. They usually are seeking for surgical procedures to correct these problems. (Hexsel D, Serra M, Mazzuco R, Dal'Forno T, Zechmeister D. *J Drugs Dermatol.* 2003 October; 2(5):511-8; Rotunda A M, Kolodney M S. *Dermatol Surg.* 2006; 32(4):465-80)

A new compound approved in the US use the deoxycholate, marketed as Kibella® by Allergan, has studies showing the efficacy and safety to administering a fat solubilizing amount of a pharmacologically active detergent composition. This method also consists of an injectable and non-surgical removal of localized fat deposits in a patient.

Small doses of triamcinolone in intralesional or local injections are largely used in dermatology for the treatment of many skin conditions, such as keloids and hypertrophic scars, and others. Intralesional corticosteroids injections release a high concentration of the drug directly on the action site, with minimal systemic absorption (Firozz, 1995) Among the many corticosteroids used for injections, triamcinolone and derivatives are more commonly used in dermatology (Firozz, 1995) and triamcinolone is the more acceptable due to its physical characteristics (Callen, 1981).

This patent application reports a new potential use of this drug in intralesional and local injections, to induce cosmetic lipoatrophy of small areas of fat accumulation on the face and beyond as well as on the body by reducing the size of the adipocytes as well as in the fat thickness.

This is a fast, efficient, cost-effective and low risk minimally invasive procedure, useful for cosmetic proposes.

What is claimed is:

1. A method of causing fat cell atrophy to decrease the size of a small fat deposit comprising the steps of:
   identifying a small fat deposit of an individual to be decreased; and
   administering, to the individual, an injectable composition comprising a corticosteroid, in the amount sufficient to cause a decrease in the size of the small fat deposit;
   wherein the step of administering comprises injecting a sufficient amount of the composition, using a needle, into the small fat deposit of the individual, to cause a decrease in the size of the small fat deposit;
   wherein the composition comprises between 1 to 9 mg of Triamcinolone acetonide as the corticosteroid in a physiologically and pharmaceutically acceptable vehicle; and
   wherein the injectable composition comprises no vasoconstrictor agent.

2. The method of claim 1 wherein the injectable composition further comprises lidocaine.

3. The method of claim 1 wherein the injectable composition comprises the triamcinolone acetonide diluted in 0.5 to 5 ml of the physiologically and pharmaceutically acceptable vehicle having a concentration of lidocaine up to 2%.

4. The method of claim 3 wherein the injectable composition comprises the concentration of lidocaine of 0.02 g/ml.

5. The method of claim 1 wherein the step of administering the composition is performed by injecting the composition into the small fat deposit on the face or body of an individual.

6. The method of claim 1 wherein the step of administering the composition is performed after a step of removing a large fat deposit by liposuction.

7. The method of claim 1 wherein the administration step is repeated every month for three months.

8. The method of claim 1 wherein the size of the small fat deposit is between 10 cubic centimeters and 30 cubic centimeters.

9. The method of claim 1 wherein the step of administering the composition results in a localized concentration of the composition.

10. The method of claim 1 further comprising the step of:
    determining a size of the small fat deposit;
    determining a dose of corticosteroid in the composition required to reduce the size of the small fat deposit; and
    administering a dose of corticosteroid of between 2 mg and 4 mg.

11. The method of claim 1 further comprising the step of determining a size of the small fat deposit;
determining a dosage of corticosteroid required to reduce the size of the small fat deposit;
selecting the amount of the solution containing the corticosteroid; and
diluting the solution with the physiological acceptable medium to form the composition.

12. A method of causing fat cell atrophy to decrease the size of a small fat deposit comprising the steps of:
identifying a small fat deposit of an individual to be decreased; and
administering, to the individual, an amount of injectable components comprising a corticosteroid and a physiological acceptable medium, the amount sufficient to cause a decrease in the size of the small fat deposit;
wherein the step of administering comprises injecting a sufficient amount of the components, using at least one needle, into the small fat deposit of the individual;
wherein the administering step comprises more than one injection of the components at different locations of the small fat deposit;
wherein a composition of the components comprises between 1 mg to 9 mg of Triamcinolone acetonide as the corticosteroid in a saline or physiological pH solution as the physiological acceptable medium, the composition further comprising lidocaine.

13. The method of claim 12 wherein the composition comprises up to 2% of lidocaine.

14. The method of claim 12 wherein the composition comprises 2 mg of lidocaine.

15. The method of claim 12 wherein the components comprises the triamcinolone acetonide diluted in 0.5 to 5 ml of the saline or physiological pH solution having a concentration of lidocaine of 0.01 g/mL to 0.02 g/mL.

16. The method of claim 12 wherein the composition comprises a concentration of 2 mg/ml of triamcinolone acetonide.

17. The method of claim 12 wherein the composition comprises between 1 to 4 mg of triamcinolone acetonide.

18. The method of claim 12 wherein the composition comprises between 1 to 2 mg of triamcinolone acetonide.

19. The method of claim 12 wherein the composition comprises no vasoconstrictor agents.

20. The method of claim 12 wherein the size of the small fat deposit is between 10 cubic centimeters and 30 cubic centimeters.

* * * * *